United States Patent
Joo et al.

(10) Patent No.: US 9,751,995 B2
(45) Date of Patent: Sep. 5, 2017

(54) SUPERABSORBENT POLYMER AND A PREPARATION METHOD THEREOF

(71) Applicant: LG CHEM, LTD., Seoul (KR)

(72) Inventors: Hyo Sook Joo, Daejeon (KR); Ki Youl Yoon, Daejeon (KR); Gi Cheul Kim, Daejeon (KR); Ju Eun Kim, Daejeon (KR); Hyeon Choi, Daejeon (KR); Hee Jung Choi, Daejeon (KR); Sung Soo Park, Daejeon (KR); Sung Hyun Park, Daejeon (KR); Myung Han Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/123,447

(22) PCT Filed: Aug. 4, 2015

(86) PCT No.: PCT/KR2015/008140
§ 371 (c)(1),
(2) Date: Sep. 2, 2016

(87) PCT Pub. No.: WO2016/021914
PCT Pub. Date: Feb. 11, 2016

(65) Prior Publication Data
US 2017/0073478 A1    Mar. 16, 2017

(30) Foreign Application Priority Data

Aug. 4, 2014  (KR) .................. 10-2014-0099700
Aug. 4, 2014  (KR) .................. 10-2014-0099701
Jun. 2, 2015   (KR) .................. 10-2015-0077872
Aug. 3, 2015  (KR) .................. 10-2015-0109701
Aug. 3, 2015  (KR) .................. 10-2015-0109702

(51) Int. Cl.
| | |
|---|---|
| C08J 3/24 | (2006.01) |
| C08J 3/075 | (2006.01) |
| C08K 3/00 | (2006.01) |
| C08K 5/00 | (2006.01) |
| A61L 15/60 | (2006.01) |
| C08F 220/06 | (2006.01) |
| A61L 15/24 | (2006.01) |
| B01J 20/26 | (2006.01) |
| B01J 20/28 | (2006.01) |
| C08F 292/00 | (2006.01) |
| C08F 222/02 | (2006.01) |

(52) U.S. Cl.
CPC .............. *C08J 3/245* (2013.01); *A61L 15/24* (2013.01); *A61L 15/60* (2013.01); *B01J 20/267* (2013.01); *B01J 20/28004* (2013.01); *B01J 20/28059* (2013.01); *B01J 20/28061* (2013.01); *B01J 20/28064* (2013.01); *C08F 220/06* (2013.01); *C08F 292/00* (2013.01); *C08J 3/075* (2013.01); *C08J 3/24* (2013.01); *C08K 3/00* (2013.01); *C08K 5/00* (2013.01); *C08F 222/02* (2013.01); *C08J 2333/02* (2013.01)

(58) Field of Classification Search
CPC .... C08J 3/24; C08J 3/245; A61L 15/24; B01J 20/26; B01J 20/267
USPC ........................................................ 502/402
See application file for complete search history.

(56) References Cited

U.S. PATENT DOCUMENTS

| | | | |
|---|---|---|---|
| 4,734,478 | A | 3/1988 | Tsubakimoto et al. |
| 5,032,628 | A | 7/1991 | Choi et al. |
| 5,140,076 | A | 8/1992 | Hatsuda et al. |
| 8,808,565 | B2 | 8/2014 | Han et al. |
| 8,815,981 | B2 | 8/2014 | Yang et al. |
| 2005/0245393 | A1 | 11/2005 | Herfert et al. |
| 2005/0250866 | A1 | 11/2005 | Champ et al. |
| 2007/0232760 | A1 | 10/2007 | Fujimaru et al. |
| 2010/0210746 | A1 | 8/2010 | Gustafson et al. |
| 2012/0157622 | A1 | 6/2012 | Lindner et al. |
| 2012/0157623 | A1 | 6/2012 | Lindner et al. |
| 2013/0261209 | A1 | 10/2013 | Kim et al. |
| 2014/0031498 | A1 | 1/2014 | Smith et al. |
| 2015/0246153 | A1 | 9/2015 | Ota et al. |
| 2015/0322180 | A1 | 11/2015 | Matsumoto et al. |

FOREIGN PATENT DOCUMENTS

| | | |
|---|---|---|
| JP | 9-77810 A | 3/1997 |
| JP | 10-7951 A | 1/1998 |

(Continued)

OTHER PUBLICATIONS

Pronoy K. Chatterjee, "Absorbency", Textile Science and Technology 7, 1985, Elsevier, pp. 42-43.

(Continued)

*Primary Examiner* — Edward Johnson
(74) *Attorney, Agent, or Firm* — Dentons US LLP

(57) ABSTRACT

The present invention relates to a superabsorbent polymer that has more improved gel strength and is improved in both water retention capacity (centrifuge retention capacity, CRC) and absorption ability under pressure (AUP) because of an optimized cross-linked structure of a base resin powder inside a cross-linked surface layer, and a preparation method thereof. The superabsorbent polymer includes a base resin powder including a 1st cross-linked polymer of a water-soluble ethylenic unsaturated monomer having acid groups of which at least a part is neutralized, and a cross-linked surface layer that includes a 2nd cross-linked polymer further cross-linked from the 1st cross-linked polymer and is formed on the base resin powder, wherein an inorganic particle is chemically bonded to the 1st cross-linked polymer by the medium of a cross-linking bond, an oxygen-containing bond (—O—), or a nitrogen-containing bond (—NR—, where R is hydrogen or a C1-C3 alkyl or an amide bond).

16 Claims, 1 Drawing Sheet

(56) References Cited

FOREIGN PATENT DOCUMENTS

| JP | 2005-532859 A | 11/2005 |
|---|---|---|
| JP | 2007-159690 A | 6/2007 |
| JP | 4255233 B2 | 4/2009 |
| JP | 2009-519356 A | 5/2009 |
| JP | 2012-12451 A | 1/2012 |
| JP | 2012-172114 A | 9/2012 |
| JP | 2013-76073 A | 4/2013 |
| JP | 5330644 B2 | 10/2013 |
| JP | 2013-255556 A | 12/2013 |
| JP | 2014-500366 A | 1/2014 |
| JP | 2014-23766 A | 2/2014 |
| JP | 2014-80547 A | 5/2014 |
| KR | 10-1991-0008293 B1 | 10/1991 |
| KR | 10-0476908 B1 | 3/2005 |
| KR | 10-0791049 B1 | 1/2008 |
| KR | 10-2010-0114052 A | 10/2010 |
| KR | 10-2011-0066902 A | 6/2011 |
| KR | 10-2011-0134333 A | 12/2011 |
| KR | 10-2012-0093088 A | 8/2012 |
| KR | 10-2012-0112474 A | 10/2012 |
| KR | 10-2013-0018350 A | 2/2013 |
| KR | 10-2013-0120424 A | 11/2013 |
| KR | 10-1348391 B1 | 1/2014 |
| KR | 10-2016-0016713 A | 2/2016 |
| KR | 10-2016-0016714 A | 2/2016 |
| WO | 2014-084281 A1 | 6/2014 |

OTHER PUBLICATIONS

"Flow of Fluids through Granular Beds and Packed Columns", Chemical Engineering, vol. II, 3rd edition, Pergamon Press, 1978, pp. 125-127.
"UV Coatings: Basics, Recent Developments and New Applications", Elsevier Science, Dec. 21, 2006, p. 115.
George Odian, "Principles of Polymerization", A Wiley-Interscience Publication, 1981, p. 203.
Office Action of Korean Patent Office in Appl'n No. 10-2015-0109702, dated Dec. 19, 2016.
Third Party Observation (TPO) dated Dec. 2, 2016 of the corresponding PCT/KR2015/008140.
International Search Report from PCT/KR2015/008140, dated Nov. 5, 2015.
Written Opinion of the ISA from PCT/KR2015/008140, dated Nov. 5, 2015.
Lee, Wen-Fu, et al., "Preparation of Reactive Mineral Powders Used for Poly(sodium acrylate) Composite Superabsorbents," Journal of Applied Polymer Science, John Wiley & Sons, Inc, US, vol. 97, No. 3, Aug. 2005, pp. 855-861.

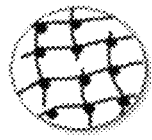
Prior (single cross-linked structure)
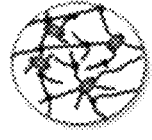
Novel (double cross-linked structure)

SUPERABSORBENT POLYMER AND A
PREPARATION METHOD THEREOF

CROSS-REFERENCE TO RELATED
APPLICATION(S)

This application is a National Stage Application of International Application No. PCT/KR2015/008140 filed on Aug. 4, 2015, which claims the benefit of Korean Patent Application No. 10-2014-0099700 filed on Aug. 4, 2014, Korean Patent Application No. 10-2014-0099701 filed on Aug. 4, 2014, Korean Patent Application No. 10-2015-0077872 filed on Jun. 2, 2015, Korean Patent Application No. 10-2015-0109701 filed on Aug. 3, 2015 and Korean Patent Application No. 10-2015-0109702 filed on Aug. 3, 2015, all of which are hereby incorporated by reference in their entirety for all purposes as if fully set forth herein.

TECHNICAL FIELD

The present invention relates to a superabsorbent polymer that has more improved gel strength and is improved in both water retention capacity (centrifuge retention capacity, CRC) and absorption ability under pressure (AUP) due to an optimized cross-linked structure of the base resin powder inside the cross-linked surface layer, and a preparation method thereof.

BACKGROUND OF THE INVENTION

A superabsorbent polymer (SAP) is a synthetic polymer material having a function of absorbing water at about 5 hundred times to about 1 thousand times its own weight, and it has been differently called a superabsorbency material (SAM), an absorbent gel material (AGM), and so on by development enterprises.

The SAP disclosed above was started to be commercialized for sanitary items, and is now being widely used as a water combination soil for horticulture, a water-stop material for civil engineering and construction, a nursery sheet, a freshness preservative in a food distribution field, a poultice material, and the like in addition to the sanitary fittings such as a disposable diaper and a sanitary napkin.

In most cases, the SAP is being widely used in the field of sanitary fittings such as disposable diapers and sanitary napkins, and, for this purpose, it needs to show high absorptivity to moisture, the moisture absorbed therein must not leak out even under external pressure, and it needs to show excellent permeability by maintaining its shape even in an expanded (swelled) state after absorbing water.

However, it has been known that the water retention capacity (centrifuge retention capacity, CRC) indicating basic absorptivity and water retention ability of the SAP and the absorption ability under pressure (AUP) indicating the characteristic of holding the absorbed moisture even under external pressure are difficult to improve together.

This is because the water retention capacity may relatively increase but the absorption ability under pressure may decrease when the overall cross-linking density of the SAP is controlled to be low, because the cross-linked structure becomes loose and the gel strength is reduced.

On the other hand, when the cross-linking density is controlled to be high for improving the absorption ability under pressure, the basic water retention capacity may decrease because it becomes a dense cross-linked structure in which it is difficult to absorb moisture.

For this reason, there was a limit in providing the SAP of which the water retention capacity and the absorption ability under pressure are improved together.

To resolve this, there have been various attempts for improving such properties together by controlling kinds of inner cross-linking agents or surface cross-linking agents or usage of the same, but such attempts have reached the limit.

Therefore, developments of an SAP showing improved water retention capacity and absorption ability under pressure together and technology enabling the preparation of the same are continuously required.

PRIOR ART DOCUMENTS

Patent Documents (Patent Document 1) Japan Patent Publication No. 2014-023766

DISCLOSURE OF INVENTION

Technical Problem

It is an aspect of the present invention to provide a superabsorbent polymer that has more improved gel strength and is improved in both of water retention capacity (CRC) and absorption ability under pressure (AUP) due to an optimized cross-linked structure of a base resin powder inside the cross-linked surface layer.

It is another aspect of the present invention to provide a preparation method of the SAP.

Technical Solution to Problem

The present invention provides a superabsorbent polymer (SAP) including a base resin powder including: a 1st cross-linked polymer of a water-soluble ethylenic unsaturated monomer having acid groups of which at least a part is neutralized; and a cross-linked surface layer that includes a 2nd cross-linked polymer that is further cross-linked from the 1st cross-linked polymer and is formed on the base resin powder, wherein an inorganic particle is chemically bonded to the 1st cross-linked polymer by the medium of a cross-linking bond, an oxygen-containing bond (—O—), or a nitrogen-containing bond (—NR—, where R is hydrogen or a $C_1$-$C_3$ alkyl or amide bond).

The present invention also provides a preparation method of a superabsorbent polymer (SAP) including the steps of: preparing a hydrogel polymer by carrying out cross-linking polymerization of a water-soluble ethylenic unsaturated monomer having acid groups of which at least a part is neutralized, in the presence of an inner cross-linking agent and an inorganic particle of which the surface is modified with a cross-linkable or hydrophilic functional group including at least one functional group selected from the group consisting of a (meth)acrylate-based functional group, an allyl group, a vinyl group, an epoxy group, a hydroxy group, an isocyanate group, and an amine group; preparing a base resin powder by drying, pulverizing, and classifying the hydrogel polymer; and forming a cross-linked surface layer by further cross-linking the surface of the base resin powder in the presence of a surface cross-linking agent.

Hereinafter, the SAP according to a specific embodiment of the invention and the preparation method thereof are explained in more detail.

However, the following is only for better understanding of the present invention, and the scope of the present invention is not limited thereby, and it is obvious to a person skilled in the related art that the embodiments can be variously modified within the scope of the present invention.

In addition, "include" or "have" means to include any elements (or components) without particular limitation unless there is a particular mention about them in this description, and it cannot be interpreted as having a meaning of excluding addition of other elements (or components).

In this description, (meth)acrylate means both an acrylate and a methacrylate.

According to one embodiment of the present invention, a superabsorbent polymer (SAP) including: a base resin powder including the 1st cross-linked polymer of a water-soluble ethylenic unsaturated monomer having acid groups of which at least a part is neutralized; and a cross-linked surface layer that includes the 2nd cross-linked polymer further cross-linked from the 1st cross-linked polymer and formed on the base resin powder, wherein an inorganic particle is chemically bonded to the 1st cross-linked polymer by the medium of a cross-linking bond, an oxygen-containing bond (—O—), or a nitrogen-containing bond (—NR—, where R is hydrogen or a $C_1$-$C_3$ alkyl or amide bond), is provided.

The present inventors recognized, from results of experiments, that the cross-linked structure of the inner part of the SAP, for example, the base resin powder inside the cross-linked surface layer, was optimized when the SAP was prepared by carrying out the cross-linking polymerization by using the inorganic particle of which the surface was modified with a cross-linkable or hydrophilic functional group including a (meth)acrylate-based functional group, an allyl group, a vinyl group, an epoxy group, a hydroxy group, an isocyanate group, an amine group, and so on, and subsequent processes, and the SAP of which the water retention capacity and the absorption ability under pressure are increased together, can be obtained, and accomplished the present invention.

In the SAP prepared in this way, for example, the polymer chains polymerized from the water-soluble ethylenic unsaturated monomer are not only cross-linked by the medium of the cross-linkable functional group of the inner cross-linking agent that has been previously used, but are also bonded by the medium of the cross-linkable or hydrophilic functional group of the inorganic particle, and form the cross-linked structure through the cross-linking bond, oxygen-containing bond (—O—), or nitrogen-containing bond derived from these functional groups.

Accordingly, the SAP of one embodiment of the invention, particularly, the base resin powder inside the cross-linked surface layer, has a novel double cross-linked structure mediated by the inner cross-linking agent and the surface-modified inorganic particle. For reference, the FIGURE schematically represents the novel double cross-linked structure of the SAP of one embodiment in comparison with the cross-linked structure of the existing SAP.

Because of the double cross-linked structure, the SAP of one embodiment can basically show high cross-linking density and relatively high gel strength, and thus it can show excellent absorption ability under pressure. Consequently, not only does the moisture absorbed in the SAP not leak out even under external pressure, but the SAP can also show excellent permeability by maintaining its shape well even in an expanded (swelled) state after absorbing water. Furthermore, the inorganic particle, for example, a silica particle or an alumina particle, occupies a certain space in the cross-linked structure in the SAP of one embodiment. On this account, in spite of said high cross-linking density, it can basically absorb and retain a large amount of moisture and can show more improved water retention capacity.

Therefore, unlike the common belief that there is an inverse relationship between the water retention capacity and the absorption ability under pressure, the SAP of one embodiment can show an excellent characteristic that both of the water retention capacity and the absorption ability under pressure are improved together due to the novel double cross-linked structure disclosed above. Therefore, the SAP of one embodiment can basically resolve the problems of existing SAPs and the technical requirements of the related art, and can show more improved properties.

Hereinafter, the structure of the SAP of one embodiment and the preparation method thereof are explained in more detail.

The SAP of one embodiment basically includes the 1st cross-linked polymer prepared by the cross-linking polymerization of the water-soluble ethylenic unsaturated monomer as the base resin powder, like prior SAPs, and includes the cross-linked surface layer formed on the base resin powder. Such cross-linked surface layer includes the 2nd cross-linked polymer that is formed by further cross-linking the 1st cross-linked polymer in the presence of a surface cross-linking agent, as an example.

In addition to this, since the inorganic particle of which the surface is modified with a cross-linkable or hydrophilic functional group disclosed above is used in company with an inner cross-linking agent that has been generally used in the polymerization process for preparing the 1st cross-linked polymer and the base resin powder of the SAP of one embodiment, the inorganic particle is chemically bonded (for example, a covalent bond, a cross-linking bond, and so on) to the polymer chains of the 1st cross-linked polymer by the medium of a cross-linking bond derived from the functional group (for example, a cross-linking bond derived from a (meth)acrylate-based functional group or a cross-linkable functional group of allyl group or vinyl group) disclosed above, or an oxygen-containing bond or nitrogen-containing bond (for example, an ether bond, an amine bond, or an amine bond derived from a hydrophilic functional group of an epoxy group, a hydroxy group, an isocyanate group, or an amine group). By this, the 1st cross-linked polymer and the base resin powder have the double cross-linked structure that is formed by the medium of the inner cross-linking agent and the surface-modified inorganic particle, and thus the SAP can exhibit excellent overall properties disclosed above (for example, the water retention capacity and the absorption ability under pressure that are increased together).

In the SAP of one embodiment, the water-soluble ethylenic unsaturated monomer may be one or more monomers selected from the group consisting of an anionic monomer of acrylic acid, methacrylic acid, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, or 2-(meth)acrylamide-2-methyl propane sulfonic acid, and a salt thereof; a nonionic hydrophilic monomer of (meth)acrylamide, N-substituted (meth)acrylate, 2-hydroxyethyl(meth)acrylate, 2-hydroxypropyl(meth)acrylate, methoxy polyethyleneglycol (meth)acrylate, or polyethyleneglycol (meth)acrylate; and an amino-containing unsaturated monomer of (N,N)-dimethylaminoethyl (meth)acrylate, or (N,N)-dimethylaminopropyl (meth)acrylamide, and a quaternary compound thereof. Among them, acrylic acid or a salt thereof, for example, acrylic acid of which at least a part is neutralized and/or an alkali metal salt, such as sodium salt, thereof may be used, and the SAP having more excellent properties can be prepared by using such monomer. In the case of using an alkali metal salt of acrylic acid as the monomer, it may be prepared by neutralizing acrylic acid with a basic compound such as sodium hydroxide (NaOH).

Furthermore, any inner cross-linking agent having a cross-linkable functional group that has been used for preparing a SAP can be used as the inner cross-linking agent for introducing the basic cross-linked structure into the 1st cross-linked polymer and the base resin powder, without limitation. However, in order to introduce a proper cross-linked structure into the 1st cross-linked polymer and the base resin powder and further improve the properties of the SAP, a multi-functional acrylate-based compound having a plurality of ethylene oxide groups may be used as the inner cross-linking agent. As more specific examples of the inner cross-linking agent, one or more compounds selected from the group consisting of polyethyleneglycol diacrylate (PEGDA), glycerin diacrylate, glycerin triacrylate, unmodified or ethoxylated trimethylol triacrylate (TMPTA), hexanediol diacrylate, and triethyleneglycol diacrylate may be used.

Also, a silica nanoparticle or an alumina nanoparticle that is surface-modified with the hydrophilic or cross-linkable functional group may be used as the surface-modified inorganic particle that is used in company with the inner cross-linking agent for preparing the 1st cross-linked polymer. Namely, the inorganic particle may be surface-modified with a cross-linkable or hydrophilic functional group including at least one functional group selected from the group consisting of a (meth)acrylate-based functional group, an allyl group, a vinyl group, an epoxy group, a hydroxy group, an isocyanate group, and an amine group, and specifically, the inorganic particle may be a silica nanoparticle or a alumina nanoparticle of which the surface is modified with a cross-linkable or hydrophilic functional group including at least one functional group selected from the group consisting of a (meth)acrylate-based functional group, an allyl group, a vinyl group, an epoxy group, a hydroxy group, an isocyanate group, and an amine group.

The cross-linkable or hydrophilic functional group may include at least one functional group selected from the group consisting of a (meth)acrylate-based functional group, an allyl group, a vinyl group, an epoxy group, a hydroxy group, an isocyanate group, and an amine group. Specifically, the cross-linkable or hydrophilic functional group may be a $C_2$-$C_{20}$ substituent including at least one functional group selected from the group consisting of a (meth)acrylate-based functional group, an allyl group, a vinyl group, an epoxy group, a hydroxy group, an isocyanate group, and an amine group at the end.

As disclosed above, the inorganic particle can be chemically bonded to the 1st cross-linked polymer by the medium of a cross-linking bond, an oxygen-containing bond (—O—), or a nitrogen-containing bond, wherein the cross-linking bond, the oxygen-containing bond (—O—), or the nitrogen-containing bond may be formed through the reaction between the 1st cross-linked polymer and the inorganic particle of which the surface is modified with the cross-linkable or hydrophilic functional group.

As an example of the inorganic particle of which the surface is modified with the cross-linkable or hydrophilic functional group, the inorganic particle of which the surface is bonded to the compound of Chemical Formula 1 may be used.

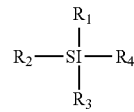

[Chemical Formula 1]

In Chemical Formula 1, $R_1$ to $R_3$ are independently a $C_1$ to $C_{10}$ alkyl group, a $C_1$ to $C_{10}$ alkoxy group, or a halogen, and at least one of them is not an alkyl group, $R_4$ is a $C_2$ to $C_{20}$ aliphatic functional group including at least one functional group selected from the group consisting of a (meth)acrylate-based functional group, an allyl group, a vinyl group, an epoxy group, a hydroxy group, an isocyanate group, and an amine group at the end, or a $C_2$ to $C_{20}$ hetero-aliphatic functional group of which at least one carbon is substituted with oxygen or nitrogen, including at least one functional group selected from the group consisting of a (meth)acrylate-based functional group, an allyl group, a vinyl group, an epoxy group, a hydroxy group, an isocyanate group, and an amine group at the end.

The aliphatic functional group means a functional group derived from an aliphatic hydrocarbon, for example, an alkane, an alkene, or an alkyne. Furthermore, the hetero-aliphatic functional group means an aliphatic functional group of which at least one carbon is substituted with a heteroatom, for example, oxygen or nitrogen.

The compound of Chemical Formula 1 may be bonded to the surface of the inorganic particle through a siloxane bond, and specifically, at least one of $R_1$ to $R_3$ is substituted with a hydroxyl group or an oxygen-containing group of the surface of the silica particle or the alumina particle so as to form the siloxane bond including the silicon particle of Chemical Formula 1.

The inorganic particle of which the surface is modified with the cross-linkable or hydrophilic functional group is preferably an inorganic particle of which the surface is modified with about 2 to 4000, or about 5 to 3000, or about 10 to 2000 cross-linkable or hydrophilic functional groups per particle. Considering a proper number of the cross-linkable or hydrophilic functional groups to be introduced per surface-modified inorganic particle, the surface-modified inorganic particle may be prepared by reacting the inorganic particle and the surface-modifying agent having the cross-linkable or hydrophilic functional group with a proper content ratio.

The number of cross-linkable or hydrophilic functional groups introduced to one surface-modified inorganic particle may be changed according to a specific functional group. For example, when the cross-linkable or hydrophilic functional group introduced to the surface of the inorganic particle is the cross-linkable or hydrophilic functional group including at least one functional group selected from the group consisting of a (meth)acrylate-based functional group, an allyl group, and a vinyl group, 2 to 500 functional groups may be introduced to the surface of one inorganic particle.

The cross-linkable or hydrophilic functional group including at least one functional group selected from the group consisting of a (meth)acrylate-based functional group, an allyl group, and a vinyl group may act as a kind of cross-linking agent, that is, if 2 or more cross-linkable or hydrophilic functional groups are connected to the surface of one inorganic particle, it may act as a cross-linking agent. However, when the cross-linkable or hydrophilic functional groups including at least one functional group selected from the group consisting of a (meth)acrylate-based functional group, an allyl group, and a vinyl group exist excessively, the surface of the modified inorganic particle may become hydrophobic, and accordingly, the transparency of the neutralization solution including the surface-modified inorganic particle may decrease, and it becomes difficult for UV rays to penetrate into the liquid and the polymerization may not occur properly when UV polymerization is carried out.

Furthermore, when the cross-linkable or hydrophilic functional group including at least one functional group selected from the group consisting of an epoxy group, a hydroxy group, an isocyanate group, and an amine group is introduced to the surface of the inorganic particle, 2 to 2000 functional groups may be connected to the surface of one inorganic particle. As the cross-linkable or hydrophilic functional group including at least one functional group selected from the group consisting of an epoxy group, a hydroxy group, an isocyanate group, and an amine group is connected to the surface of the modified inorganic particle, the neutralization solution including the surface-modified inorganic particle may have higher dispersion stability and transparency, and the phenomenon that the surface-modified inorganic particles cohere in the neutralization solution may be prevented.

In more specific examples, a silica nanoparticle such as fumed silica or colloidal silica may be representatively used as the surface-modified inorganic particle. Furthermore, the amount of the cross-linkable or hydrophilic functional group per unit area of the surface-modified inorganic particle may be 00.004 μmol/m² or more.

In the case of the fumed silica, the inorganic particle and the surface modifying agent may be reacted so that the amount of the cross-linkable or hydrophilic functional group per surface area of 1 m² of the silica nanoparticle becomes about 0.004 μmol/m² or more, about 0.04 μmol/m² or more, about 1.0 μmol/m² or more, or about 0.04 to 4 μmol/m².

In the case of the colloidal silica, the inorganic particle and the surface modifying agent may be reacted so that the amount of the cross-linkable or hydrophilic functional group per surface area of 1 m² of the silica nanoparticle becomes about 0.004 μmol/m² or more, about 0.07 μmol/m² or more, about 1.0 μmol/m² or more, or about 0.07 to 7 μmol/m².

The amount of the cross-linkable or hydrophilic functional group per unit area of the surface-modified inorganic particle may be changed according to a specific functional group.

For example, the amount of the cross-linkable or hydrophilic functional groups including at least one functional group selected from the group consisting of a (meth)acrylate-based functional group, an allyl group, and a vinyl group per unit area of the surface-modified inorganic particle may be 0.004 to 0.8 μmol/m².

Furthermore, the amount of the cross-linkable or hydrophilic functional group including at least one functional group selected from the group consisting of an epoxy group, a hydroxy group, an isocyanate group, and an amine group per unit area of the surface-modified inorganic particle may be 0.04 to 4.0 μmol/m².

The degree of surface modification may be calculated based on the following TGA (thermal gravimetric analysis) results.

Calculation of TGA loss according to the surface modification (theoretic weight reduction) [Equation 1]

$$T(TGA\ Loss\ \%) = A \times \frac{C}{(100 + B \times C)} \times 100\%$$

A: weight ratio of the thermal-degraded surface modifying agent

B: weight ratio of the component remained after sol-gel reaction between the surface modifying agent and the silica C: weight (g) of the surface modifying agent involved in the surface modification per 100 g of the silica By using the above equation, the weight of the surface modifying agent involved in the surface modification (C) can be represented by the following Equation 2.

$$C(g) = \frac{100 \times T}{(100 + A - B \times T)} \quad [\text{Equation 2}]$$

At this time, the amount of the surface modifying agent modified per unit area (D) may be calculated as in the following Equation 3.

$$D(\mu mol/m2) = \frac{\frac{C}{M} \times 10^6}{100 \times BET} \quad [\text{Equation 3}]$$

M: molecular weight of the surface modifying agent
BET: specific surface are of the silica used (m²/g)

For example, when the specific surface area of silica particle is 200 m²/g, the surface modifying agent is GPTMS (MW=236.34 g/mol), and TGA loss (200° C. to 800° C. section) is 3 wt %, the weight (g) of the surface modifying agent involved in the surface modification per 100 g of the silica (C) is 6.42 g and the amount of the surface modifying agent modified per unit area (D) is 1.36 μmol/m².

Further the surface-modified inorganic particle may have a specific surface area of about 5 to 600 m²/g and a diameter of about 5 to 500 nm. Because of the particle size, a double cross-linked structure is properly formed in the final SAP prepared and the inorganic particle occupies a space of a proper volume in the cross-linked structure, and thus the SAP can show excellent water retention capacity in company with excellent absorption ability under pressure.

The amount of the inorganic particle bonded to the base resin powder may be about 0.01 to 30 parts by weight based on 100 parts by weight of the base resin powder. In this way, the double cross-linked structure is optimally introduced to the base resin powder and the 1st cross-linked polymer, and thus the SAP of one embodiment can have more improved properties, for example, the water retention capacity and the absorption ability under pressure. Meanwhile, details of the kind of the surface-modified inorganic particle, the preparation method thereof, and the method of introducing the same will be explained in more detail in the section regarding the preparation method disclosed below.

Furthermore, in the SAP of one embodiment disclosed above, any surface cross-linking agent that has been used for preparing a SAP can be used as the surface cross-linking agent for forming the cross-linked surface layer formed on the base resin powder and the 2nd cross-linked polymer included therein, without limitation. For more specific examples, one or more compounds selected from the group consisting of ethyleneglycol, 1,4-butanediol, 1,6-hexanediol, polypropyleneglycol, 1,2-hexanediol, 1,3-hexanediol, 2-methyl-1,3-propanediol, 2,5-hexanediol, 2-methyl-1,3-pentanediol, 2-methyl-2,4-pentanediol, tripropyleneglycol, glycerol, ethylene carbonate, and propylene carbonate may be used.

Further, the SAP of one embodiment disclosed above can show the characteristic that the centrifuge retention capacity (CRC) to a saline solution is about 20 to 40 g/g, the absorption ability under pressure (0.7 psi) (AUP) to a saline solution is about 15 to 35 g/g, and the gel strength is about 4000 to 20,000 Pa.

The SAP of one embodiment disclosed above can show excellent water retention capacity in company with more improved gel strength and absorption ability under pressure because of the novel double cross-linked structure introduced into the base resin powder inside the cross-linked surface layer. Therefore, the SAP can be adequately applied to various sanitary fittings such as a diaper, and can show excellent overall properties.

Meanwhile, the centrifuge retention capacity (CRC) to a saline solution may be measured according to EDANA method WSP 241.2. More specifically, the centrifuge retention capacity can be calculated by the following Calculation Equation 1, after making the SAP absorb saline solution for 30 min.

$$CRC(g/g)=\{[W_2(g)-W_1(g)]/W_0(g)\}-1 \quad \text{[Calculation Equation 1]}$$

In Calculation Equation 1, $W_0(g)$ is the initial weight (g) of the SAP, $W_1(g)$ is the weight of the apparatus measured after dehydrating the same by using a centrifugal separator at 250 G for 3 min without using the SAP, and $W_2(g)$ is the weight of the apparatus with the SAP measured after soaking the SAP in a 0.9 wt % saline solution for 30 min at room temperature and dehydrating the same by using a centrifugal separator at 250 G for 3 min.

Furthermore, the absorption ability under pressure (0.7 psi) (AUP) may be measured according to EDANA method WSP 242.2. More specifically, the absorption ability under pressure can be calculated by the following Calculation Equation 2, after making the SAP absorb saline solution for 1 h under the pressure of about 0.7 psi.

$$AUP(g/g)=[W_4(g)-W_3(g)]/W_0(g) \quad \text{[Calculation Equation 2]}$$

In Calculation Equation 2, $W_0(g)$ is the initial weight (g) of the SAP, $W_3(g)$ is a sum of the weight of the SAP and the weight of the apparatus providing load to the SAP, $W_4(g)$ is a sum of the weight of the SAP and the weight of the apparatus providing load to the SAP measured after making the SAP absorb saline solution for 1 h under the pressure (0.7 psi).

$W_0(g)$ in Calculation Equations 1 and 2 corresponds to the initial weight of the SAP before the SAP absorbs a saline solution, and it may be same or different in said equations.

Further, the horizontal direction gel strength G' may be measured according to the following method disclosed in Korea Patent Application No. 2014-01653514.

More specifically, after making the SAP absorb the saline solution for 1 h, the horizontal direction gel strength G' may be measured according to the method including the following steps, by using a commercial rheometer.

1) The step of making the SAP absorb the saline solution and swell; 2) the step of positioning the swelled SAP between the plates of the rheometer having a certain gap and pressing both sides of the plates; 3) the step of checking the shear strain in the linear viscoelastic regime section where the storage modulus and the loss modulus are uniform, while increasing the shear strain by using the rheometer under vibration; and 4) the step of measuring the storage modulus and the loss modulus of the swelled SAP under the checked shear strain and determining the average value of the storage modulus as the gel strength.

More specific measuring conditions and method of the horizontal direction gel strength G' are disclosed in examples below.

In addition, in the SAP of one embodiment, the permeability (SFC) to the saline solution under the pressure of about 0.3 psi may be about $10 \times 10^{-7}$ cm$^3$*s/g or more. The permeability may be measured according to a method using Darcy's law and a constant flow method (for example, "Absorbency", edited by P. K. Chatterjee, Elsevier 1985, pp. 42-43, and Chemical Engineering, Vol. II, 3rd edition, J. M. Coulson and J. F. Richardson, Pergamon Press, 1978, pp. 125-127).

The SAP of one embodiment disclosed above may have the shape of a particle such as a spherical particle or an amorphous particle having a diameter of about 150 to 850 µm.

According to another embodiment of the invention, the method of preparing the SAP including the steps of: preparing a hydrogel polymer by carrying out cross-linking polymerization of a water-soluble ethylenic unsaturated monomer having acid groups of which at least a part is neutralized, in the presence of an inner cross-linking agent and an inorganic particle of which the surface is modified with a cross-linkable or hydrophilic functional group including at least one functional group selected from the group consisting of a (meth)acrylate-based functional group, an allyl group, a vinyl group, an epoxy group, a hydroxy group, an isocyanate group, and an amine group; preparing a base resin powder by drying, pulverizing, and classifying the hydrogel polymer; and forming a cross-linked surface layer by further cross-linking the surface of the base resin powder in the presence of a surface cross-linking agent, may be provided.

In the preparation method of such another embodiment, the SAP may be prepared by carrying out the cross-linking polymerization of the water-soluble ethylenic unsaturated monomer by using the inorganic particle of which the surface is modified with the cross-linkable or hydrophilic functional group in company with a common inner cross-linking agent, and successively carrying out the processes of drying, pulverization, classification, and surface cross-linking, according to a common preparation method of a SAP. Accordingly, the base resin powder to which the double cross-linked structure disclosed above is introduced can be prepared by using the surface-modified inorganic particle in the polymerization, and the SAP of one embodiment can be prepared therefrom.

Hereinafter, the surface-modified inorganic particle and the preparation method thereof are first concretely explained, and the preparation method of the SAP using the same is briefly explained step by step, because the preparation method of such embodiment may follow a common preparation method of a SAP except that the surface-modified inorganic particle is used in the polymerization.

The surface-modified inorganic particle may be prepared by the reaction of the surface-modifying agent having the cross-linkable or hydrophilic functional group at the end and the inorganic particle such as a silica nanoparticle or an alumina nanoparticle. At this time, any compound having the cross-linkable or hydrophilic functional group disclosed above at the end may be used as the surface modifying agent without limitation.

As an example of the surface modifying agent, at least one compound selected from the group consisting of 4-aminobutyltriethoxysilane, 4-amino-3,3-dimethylbutylmethyldimethoxylsilane, 4-amino-3,3-dimethylbutyltrimethoxysilane, N-(2-aminoethhyl)-3-aminopropylmethyldimethoxysilane, N-(2-aminoethyl)-3-aminoproylsilanetriol, N-(2-aminoethyl)-3-aminopropyltriethoxysilane, N-(2-aminoethyl)-3- aminopropyltriethoxysilane, N-(2-aminoethyl)-11-aminoundecyltriethoxysilane, N-(2-aminohexyl) aminomethyltriethoxysilane, 3-(aminophenoxy) propyltriethoxysilane, m-aminophenyltriethoxysilane, p-aminophenyltriethoxysilane, 3-aminopropylmethyldiethoxysilane, 3-aminopropylethoxysilane, 3-aminopropyletrimethoxysilane, 2-cyanoethyltriethoxysilane, 2-(3,4-epoxycyclohexyl)ethyltriethoxysilane, 2-(3,4-epoxycyclohexyl)ethyltrimethoxysilane, 5,6-epoxyhexyltriethoxysilane, (3-glycidoxypropyl) methyldiethoxysilane, (3-glycidoxypropyl)triethoxysilane, (3-slycicoxypropyl)trimethoxysilane, [hydroxyl(polyethylenoxy)propyl]triethoxysilane, N-(triethoxysiylpropyl)-opolyethylene oxide urethane, ureidopropyltriethoxysilane, 3-(triethoxysilyl)propylisocyanate, (isocyanatomethyl) methyldimethoxysilane, and 3-isocyanatopropyltrimethoxysilane may be used.

Details about the inorganic particle and the cross-linkable or hydrophilic functional group including at least one functional group selected from the group consisting of a (meth) acrylate-based functional group, an allyl group, a vinyl group, an epoxy group, a hydroxy group, an isocyanate group, and an amine group for modifying the surface thereof are the same as in the SAP of one embodiment of the invention disclosed above.

In the preparation method of the SAP of another embodiment, the hydrogel polymer may be formed by carrying out the cross-linking polymerization of the water-soluble ethylenic unsaturated monomer having acid groups of which at least a part is neutralized, in the presence of the inner cross-linking agent and the surface-modified inorganic particle disclosed above.

Additional explanations regarding the surface-modified inorganic particle, the inner cross-linking agent, and the kind and structure of the water-soluble ethylenic unsaturated monomer are omitted here because they are the same as described above.

Further, the concentration of the water-soluble ethylenic unsaturated monomer in the monomer composition including the water-soluble ethylenic unsaturated monomer, the surface-modified inorganic particle, and the inner cross-linking agent may be about 20 to about 60 wt %, or about 40 to 50 wt %, based on the entire monomer composition including the above raw materials and solvent, and a proper concentration may be selected by considering polymerization time and reaction conditions. However, when the concentration of the monomer is excessively low, there may be a problem in economy because the yield of the SAP becomes low, and contrarily, when the concentration is excessively high, there may be a problem in the process in that part of the monomer is extracted or the pulverizing efficiency becomes low in the pulverization process of the polymerized hydrogel polymer, and the properties of the SAP may decrease.

Furthermore, the monomer composition may further include a polymerization initiator that has been generally used for preparing a SAP.

Specifically, the polymerization initiator may be an initiator for thermal polymerization or an initiator for photopolymerization by UV radiation according to the polymerization method. However, even when the photopolymerization method is applied thereto, a certain amount heat is generated by UV radiation and the like, and some heat occurs as the polymerization reaction, an exothermal reaction, progresses. Therefore, the composition may additionally include the initiator for thermal polymerization.

Here, any compound which can form a radical by light such as UV rays may be used as the initiator for photopolymerization without limitation.

For example, the initiator for photopolymerization may be one or more compounds selected from the group consisting of benzoin ether, dialkyl acetophenone, hydroxyl alkylketone, phenyl glyoxylate, benzyl dimethyl ketal, acyl phosphine, and α-aminoketone. Further, as the specific example of acyl phosphine, commercial Lucirin TPO, namely, 2,4,6-trimethyl-benzoyl-trimethyl phosphine oxide, may be used. More various photoinitiators are well disclosed in "UV Coatings: Basics, Recent Developments and New Application (Elsevier, 2007)" written by Reinhold Schwalm, p 115, and the present invention is not limited to or by said examples.

The concentration of the initiator for photopolymerization in the monomer composition may be about 0.01 to about 1.0 wt %. When the concentration of the initiator for photopolymerization is excessively low, the polymerization rate becomes slow, and when the concentration of the initiator for photopolymerization is excessively high, the molecular weight of the SAP becomes low and the properties may be uneven.

Furthermore, as the initiator for thermal polymerization, one or more initiators selected from the group consisting of a persulfate-based initiator, an azo-based initiator, hydrogen peroxide, and ascorbic acid may be used. Specifically, sodium persulfate ($Na_2S_2O_8$), potassium persulfate ($K_2S_2O_8$), ammonium persulfate ($(NH_4)_2S_2O_8$), and so on may be used as examples of the persulfate-based initiators; and 2,2-azobis-(2-amidinopropane)dihydrochloride, 2,2-azobis-(N,N-dimethylene)isobutyramidinedihydrochloride, 2-(carbamoylazo)isobutylonitril, 2,2-azobis-[2-(2-imidazolin-2-yl)propane]dihydrochloride, 4,4-azobis-(4-cyanovaleric acid), and so on may be used as examples of azo-based initiators. More various initiators for thermal polymerization are well disclosed in "Principle of Polymerization (Wiley, 1981)" written by Odian, p 203, and the present invention is not limited to or by said examples.

The concentration of the initiator for thermal polymerization included in the monomer composition may be about 0.001 to about 0.5 wt %. When the concentration of the initiator for thermal polymerization is excessively low, additional thermal polymerization hardly occurs and there may be less effect according to the addition of the initiator for thermal polymerization, and when the concentration of the initiator for thermal polymerization is excessively high, the molecular weight of the SAP becomes low and the properties may be uneven.

The kind of the inner cross-linking agent included together in the monomer composition is the same as above, and the inner cross-linking agent may be included in the monomer composition with the concentration of about 0.01 to about 0.5 wt % and cross-links the prepared polymer. Particularly, the SAP satisfying the properties of one embodiment disclosed above can more properly be obtained by using about 0.3 parts by weight or more, or about 0.3 to 0.6 parts by weight, of the inner cross-linking agent, based on 100 parts by weight of the monomer, for example, non-neutralized acrylic acid.

Furthermore, the monomer composition may further include an additive such as a thickener, a plasticizer, a preservation stabilizer, an antioxidant, and so on with necessity.

The monomer composition solution may be prepared by dissolving the raw materials such as the water-soluble ethylenic unsaturated monomer, the surface-modified inorganic particle, the initiator for photopolymerization, the initiator for thermal polymerization, the inner cross-linking agent, and the additive in a solvent.

At this time, any solvent which can dissolve said components may be used without limitation, and for example, one or more solvents selected from water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butyrolactone, carbitol, methylcellosolve acetate, N,N-dimethylacetamide, and so on may be used solely or in combination.

The solvent may be included in the monomer composition at a residual quantity except for the above components.

Meanwhile, the method of preparing the hydrogel polymer by thermal polymerization or photopolymerization of the monomer composition is not particularly limited if it is a common polymerization method.

Specifically, the polymerization method is largely divided into the thermal polymerization and the photopolymerization according to the energy source of the polymerization. In the case of thermal polymerization, it is generally carried out in a reactor having a kneading spindle, such as a kneader, and in the case of photopolymerization, it may be carried out in a reactor equipped with a movable conveyor belt. However, said polymerization method is just an example, and the present invention is not limited to or by the polymerization method disclosed above.

For example, in the case of carrying out the thermal polymerization by providing hot air to a reactor such as a kneader equipped with a kneading spindle or heating the reactor, the hydrogel polymer discharged from the outlet of the reactor may have a size of centimeters or millimeters, according to the shape of the kneading spindle installed in the reactor. Specifically, the size of the obtained hydrogel polymer may vary according to the concentration and the feeding speed of the monomer composition, and generally the obtained hydrogel polymer may have a weight average diameter of about 2 to about 50 mm.

Furthermore, in the case of carrying out the photopolymerization in a reactor equipped with a movable conveyor belt, the hydrogel polymer may be obtained in the form of a sheet having a width corresponding to a width of the belt. At this time, the thickness of the polymer sheet may vary according to the concentration and the feeding speed of the monomer composition, but it is preferable to feed the monomer composition so that a polymer sheet having a thickness of about 0.5 to about 5 cm can be obtained. It is undesirable to feed the monomer composition so that the thickness of the polymer sheet becomes excessively thin, because it makes the production efficiency low, and if the thickness of the obtained polymer sheet is over 5 cm, the polymerization reaction cannot evenly occur across the thickness because of its excessively thick thickness.

Generally, the moisture content of the hydrogel polymer obtained by above method may be about 40 to about 80 wt %. At this time, "moisture content" in the present description is the content of moisture in the entire weight of the hydrogel polymer, and it means a value of which the weight of the dried polymer is subtracted from the weight of the hydrogel polymer. Specifically, the moisture content is defined as a value calculated from the weight loss due to moisture evaporation from the polymer in the process of increasing the temperature of the polymer and drying the same through infrared heating. At this time, the drying condition for measuring the moisture content is that the temperature is increased to about 180° C and maintained at 180° C., and the total drying time is 20 min (including 5 min of a heating step).

Further, after the cross-linking polymerization of the monomer, the base resin powder may be obtained by the processes of drying, pulverization, classification, and so on. Here, it is preferable that the base resin powder and the SAP obtained therefrom are prepared and provided so as to have a diameter of about 150 to 850 μm, through the processes of pulverization and classification. More specifically, at least about 95 wt % of the base resin powder and the SAP obtained therefrom have a diameter of about 150 to 850 μm, and the fine powder having a diameter less than about 150 μm may be less than about 3 wt %.

Since the particle size distributions of the base resin powder and the SAP are regulated in a preferable range in this way, the final SAP prepared can exhibit the properties disclosed above as well as excellent permeability.

The processes of drying, pulverization, and classification are more specifically explained as follows.

First, in drying the hydrogel polymer, a coarse grinding step may be further included before the drying step for increasing the drying efficiency with necessity.

At this time, the grinding machine used is not particularly limited. Specifically, it may include at least one grinding machine selected from the group consisting of a vertical pulverizer, a turbo cutter, a turbo grinder, a rotary cutter mill, a cutter mill, a disc mill, a shred crusher, a crusher, a chopper, and a disc cutter, but it is not limited to or by said examples.

In the coarse grinding step, the hydrogel may be crushed to have a diameter of about 2 to about 10 mm.

It is technically difficult to grind the hydrogel to have a diameter of less than 2 mm because of its high moisture content, and there may be a phenomenon that the crushed particles cohere with each other. Meanwhile, when the polymer is crushed to have a diameter of larger than 10 mm, the efficiency enhancing effect in the subsequent drying step may be small.

The hydrogel polymer just after the polymerization that is or is not coarse-ground as disclosed above is dried. At this time, the drying temperature of the drying step may be about 150 to about 250° C. When the drying temperature is blow about 150° C., the drying time may become excessively long and the properties of the SAP finally prepared may decrease, and when the drying temperature is over about 250° C., the surface of the polymer is excessively dried, and fine powders may be generated in the subsequent pulverization process and the properties of the SAP prepared finally may decrease. Therefore, the drying process may be preferably carried out at the temperature of about 150 to about 200° C., more preferably at the temperature of about 160 to about 180° C.

Furthermore, the drying time may be about 20 to about 90 min by considering the process efficiency, but it is not limited to this.

The drying method in the drying step is not particularly limited if it has been generally used in the drying process of the hydrogel polymer. Specifically, the drying step may be carried out by the method of hot air provision, infrared radiation, microwave radiation, UV ray radiation, and so on. The moisture content of the polymer after the drying step may be about 0.1 to about 10 wt %.

Subsequently, the step of pulverizing the dried polymer obtained from the drying step is carried out.

The polymer powder obtained after the pulverization step may have a diameter of about 150 to about 850 μm. In order to pulverize the polymer into such diameter, a pin mill, a hammer mill, a screw mill, a roll mill, a disc mill, or a jog mill may be used as the pulverizer, but it is not limited to or by said examples.

Further, in order to maintain the properties of the SAP powder that is finally commercialized after the pulverization step, a separate process of classifying the polymer powders obtained after the pulverization according to the particle size is carried out. Preferably, after classifying the polymer having the diameter of about 150 to about 850 μm, only the polymer powder may be commercialized after the surface cross-linking reaction step. Since details regarding the particle size distribution of the base resin powder obtained by this process are already explained above, more detailed explanation thereof is omitted here.

After preparing the base resin powder, the cross-linked surface layer may be formed by further cross-linking the surface of the base resin powder in the presence of the surface cross-linking agent, and the SAP may be thereby prepared. A more detailed explanation about this is omitted here because details regarding the surface cross-linking agent are already explained above.

In the surface cross-linking process, the surface cross-linked structure of the SAP may be more optimized by carrying out the surface cross-linking after adding a multi-valent metal cation in company with the surface cross-linking agent. This may be because the metal cation forms a chelate with a carboxyl group (COOH) of the SAP and further reduces the cross-linking distance.

The method of adding the surface cross-linking agent to the base resin powder is not particularly limited. For example, a method of adding and mixing the surface cross-linking agent and the base resin powder in a reactor, a method of spraying the surface cross-linking agent on the base resin powder, and a method of continuously mixing the surface cross-linking agent and the base resin powder while providing them to a continuously operating mixer may be used.

When the surface cross-linking agent is added thereto, water and methanol may be further mixed therewith. When water and methanol are added thereto, there is an advantage that the surface cross-linking agent can be evenly dispersed in the base resin powder. At this time, the amount of water and methanol per 100 parts by weight of the base resin powder may be regulated for the purposes of inducing a uniform dispersion of the surface cross-linking agent, preventing an agglomeration phenomenon, and optimizing the surface penetration depth of the cross-linking agent.

The surface cross-linking reaction may be carried out by heating the base resin powder to which the surface cross-linking agent is applied at about 160° C. or more for 20 min. Particularly, in order to obtain the SAP satisfying the properties according to one embodiment properly, the surface cross-linking process may be carried out under the condition that the maximum reaction temperature is about 180 to 200° C. and the maximum reaction temperature is maintained for about 20 min or more, or for about 20 min to 1 h. Furthermore, the heat-up time from the reaction initiation temperature, for example, about 160° C. or more, or about 160 to 170° C., to the maximum reaction temperature may be regulated to be about 10 min or more, or about 10 min to 1 h, and it is recognized that the SAP satisfying the properties according to one embodiment properly can be prepared by satisfying the above surface cross-linking process condition.

The heating means for the surface cross-linking reaction is not particularly limited. It is possible to provide a thermal media thereto or provide a heat source directly thereto. At this time, usable thermal media may be a heated fluid such as steam, hot air, hot oil, and the like, but the present invention is not limited to or by them. Furthermore, the temperature of the thermal media provided thereto may be properly selected by considering the means of the thermal media, heating speed, and target temperature of heating. Meanwhile, the heating method for providing the heat source directly thereto may be a heating method using electricity or a heating method using a gas fuel, but the present invention is not limited to or by them.

The SAP obtained by the above preparation method can show excellent properties in which various properties such as water retention capacity and absorption ability under pressure are improved together, and it can be adequately applied to various sanitary fittings such as a diaper and can show excellent overall properties.

Advantageous Effects of the Invention

According to the present invention, the SAP showing excellent characteristics such that various properties such as water retention capacity and absorption ability under pressure are improved together, unlike common sense that there is an inverse relationship between the water retention capacity and the absorption ability under pressure, and the preparation method thereof can be provided.

The SAP of the present invention basically resolves the problems of existing SAPs and the technical requirements of the related art and can show more improved properties, and can be very preferably applied to various sanitary items.

BRIEF DESCRIPTION OF THE DRAWINGS

The FIGURE schematically represents the novel double cross-linked structure of the SAP of one embodiment in comparison with the cross-linked structure of existing SAPs.

DETAILED DESCRIPTION OF THE EMBODIMENT

Below, the present invention will be described in more detail with reference to examples. However, these examples are provided only for purpose of illustrating the present invention, and should not be construed as limiting the present invention by the examples.

Example 1

The aqueous monomer composition was prepared by mixing 100 g of acrylic acid, 1,000 ppm of polyethyleneglycol diacrylate (Mw=523) as the inner cross-linking agent, 1 g of silica particles of which the surface was modified with a hydroxy group (colloidal silica of which the particle diameter was 12 nm and the specific surface area was 200 $m^2/g$), 83.3 g of 50% sodium hydroxide (NaOH), and 89.8 g of water, so that the concentration of the monomer was 45 wt %.

Subsequently, 810 g of the aqueous monomer solution was mixed with 30.54 g of a 0.18% ascorbic acid solution and 33 g of a 1% sodium persulfate solution, and the polymerization was carried out after putting the mixture and 30.45 g of a 0.15% hydrogen peroxide solution together therewith into a feeding zone of a polymerization reactor that can knead while polymerizing the same. At this time, the temperature of the polymerization reactor was maintained at 80° C., the maximum temperature of the polymerization was 110° C. and the polymerization time was 1 min 15 s. After that, the mixture was continuously kneaded, and it was polymerized and kneaded for 20 min. Consequently, the prepared polymer had the size of 0.2 cm or less. The moisture content of the finally formed hydrogel polymer was 51 wt %.

Subsequently, the hydrogel polymer was dried with a hot air drier at 180° C. for 30 min, and the dried hydrogel polymer was pulverized with a pin mill pulverizer. The polymer having a diameter less than about 150 μm and the polymer having a diameter of about 150 μm to 850 μm were classified by using a sieve.

A surface-treating solution including 5 wt % of 1,3-propanediol and 5 wt % of propylene glycol was then sprayed on the prepared base resin powder, and the mixture was stirred so that the surface-treating solution was evenly distributed on the base resin powder. The base resin powder was then put in a surface cross-linking reactor adjusted to about 190° C. and the surface cross-linking reaction was carried out. In this surface cross-linking reactor, it was recognized that the temperature of the base resin powder was slowly elevated at the initial temperature around about 160° C. and it reached the maximum reaction temperature of about 185° C. after about 30 min. After the temperature reached the maximum reaction temperature, the reaction was further carried out for about 30 min and a finally prepared SAP sample was taken. After the surface cross-linking process, the surface cross-linked SAP of which the diameter was about 150 to 850 μm was obtained by using a sieve. The content of the fine powder having the diameter of about 150 μm or less included in the SAP product was less than about 2 wt %.

Example 2

The SAP of Example 2 was obtained according to the same method as in Example 1, except that 3400 ppm of polyethyleneglycol diacrylate (Mw=523) and 0.1 g of silica particles of which the surface was modified with a hydroxy group (colloidal silica of which the particle diameter was 12 nm and the specific surface area was 200 m$^2$/g) were used. The content of the fine powder having the diameter of about 150 μm or less included in the SAP product was less than about 2 wt %.

Example 3

The SAP of Example 3 was obtained according to the same method as in Example 2, except that 0.27 g of the silica particles of which the surface was modified with a hydroxy group was used. The content of the fine powder having a diameter of about 150 μm or less included in the SAP product was less than about 2 wt %.

Example 4

The SAP of Example 4 was obtained according to the same method as in Example 3, except that 1 g of the silica particle of which the surface was modified with a hydroxy group was used. The content of the fine powder having a diameter of about 150 μm or less included in the SAP product was less than about 2 wt %.

Example 5

(1) Modification of the Silica Surface
Na$^+$ ions included in Ludox LS (colloidal silica of which the particle diameter is 12 nm and the specific surface area is 215 m$^2$/g, with a silica content 30 wt %) as a stabilizer was eliminated therefrom by using a cation exchange resin (Amberjet 1200 hydrogen form, Aldrich Co.). 30 g of isopropyl alcohol and 2 g of 3-methacryloxypropyl trimethoxysilane (3-MPTMS) were put into 100 g of said Ludox LS.

The surface modification was carried out by stirring said solution at 50° C. for 12 h or more. After washing the product with acetone, the amount of modification was obtained by measuring TGA and calculating TGA loss as in Equation 1.

Calculation of TGA loss according to the surface modification (theoretic weight reduction) [Equation 1]

$$T(TGA\ Loss\ \%) = A \times \frac{C}{(100 + B \times C)} \times 100\%$$

A: weight ratio of the thermal-degraded surface modifying agent
B: weight ratio of the component remaining after sol-gel reaction between the surface modifying agent and the silica
C: weight (g) of the surface modifying agent involved in the surface modification per 100 g of the silica (2) Preparation of the SAP
The SAP of Example 5 was obtained according to the same method as in Example 1, except that 5 g of the silica particles of which the surface was modified with 3-MPTMS was used. The content of the fine powder having a diameter of about 150 μm or less included in the SAP product was less than about 2 wt %.

Example 6

The SAP of Example 6 was obtained according to the same method as in Example 5, except that the surface-modified silica was prepared by using 4.5 g of 3-methacryloxypropyl trimethoxysilane instead of 2 g of 3-methacryloxypropyl trimethoxysilane.

Example 7

(1) Modification of the Silica Surface
After introducing 1 ml of acetic acid to 100 g of the solution prepared by dispersing 5 wt % of Aerosil 200 (fumed silica of which the particle diameter is 12 nm and the specific surface area is 200 m$^2$/g, Evonik Co.) in water and adjusting its pH 3, 2 g of 3-glycidyloxypropyl trimethoxysilane (3-GPTMS) was added thereto. After putting 70 g of beads (zirconium oxide) having a diameter of about 1 mm in the solution to which 3-GPTMS was added, the surface modification of the silica particle was carried out while mixing the same for 24 h. After the surface modification process was terminated, the obtained silica was washed with n-butyl acetate, and the amount of modification was calculated according to Equation 1 disclosed in Example 5.

(2) Preparation of the SAP
The SAP of Example 7 was obtained according to the same method as in Example 1, except that 5 g of the silica particle of which the surface was modified with 3-GPTMS was used. The content of the fine powder having a diameter of about 150 μm or less included in the SAP product was less than about 2 wt %.

Example 8

The SAP of Example 8 was obtained according to the same method as in Example 7, except that the surface-modified silica was prepared by using 6 g of 3-glycidyloxy-propyl trimethoxysilane instead of 2 g of 3-glycidyloxypropyl trimethoxysilane

Example 9

The SAP of Example 9 was obtained according to the same method as in Example 7, except that the surface-modified silica was prepared by using 1 g of 3-glycidyloxy-propyl trimethoxysilane instead of 2 g of 3-glycidyloxypropyl trimethoxysilane.

Example 10

The SAP of Example 10 was obtained according to the same method as in Example 7, except that the surface-modified silica was prepared by using 3 g of 3-glycidyloxy-propyl trimethoxysilane instead of 2 g of 3-glycidyloxypropyl trimethoxysilane.

Comparative Example 1

The SAP of Comparative Example 1 was obtained according to the same method as in Example 1, except that the silica particles of which the surface was modified with hydroxy group were not used. The content of the fine powder having the diameter of about 150 μm or less included in the SAP product was less than about 2 wt %.

Comparative Example 2

The SAP of Comparative Example 2 was obtained according to the same method as in Example 2, except that the silica particles of which the surface was modified with hydroxy group were not used. The content of the fine powder having the diameter of about 150 μm or less included in the SAP product was less than about 2 wt %.

Comparative Example 3

The experiment was carried out according to the same method as in Example 5, except that silica particles (Aerosil 200) of which the surface was not modified were used.

EXPERIMENTAL EXAMPLES

The properties of the SAPs of the examples and comparative examples were evaluated according to the following methods, and the measured property values are shown in the following Table 1.

(1) Identifying the Amount of Surface Modification by Using TGA

Regarding the surface-modified silica prepared in Examples 5 to 10 and Comparative Example 3, the weight loss of the surface-modified silica was measured in a 200 to 800° C. section by using TGA (thermogravimetric analysis), and the amount of surface modification was identified. The results are listed in the following Table 1.

TABLE 1

| | TGA Loss (%) | Cross-linkable functional group (3-MPTMS) Amount of surface modification (μmol/m$^2$) | Hydrophilic functional group (3-GPTMS) Amount of surface modification (μmol/m$^2$) |
|---|---|---|---|
| Example 5 | 1.0 | 0.37 | 0 |
| Example 6 | 2.1 | 0.80 | 0 |
| Example 7 | 5 | 0 | 2.35 |
| Example 8 | 4.3 | 0 | 1.98 |
| Example 9 | 3.1 | 0 | 1.49 |
| Example 10 | 2.1 | 0 | 0.95 |
| Comparative Example 3 | 0 | 0 | 0 |

(2) Identifying the Transparency

The solutions prepared in the examples and comparative examples were used. The transparency of the solution was measured by passing light of 470 nm through the solution with a 2 mm thickness.

(3) Identifying the Sedimentation Rate

The neutralization solutions prepared in the examples and comparative examples were used. After putting 0.4 ml of a solution prepared by adding 5% of silica to the neutralization solution in a polyamide cell with a 2 mm thickness, it was spun at 1,000 rpm by using a Lumisizer (LUM GmbH Co.). The rate of silica precipitated by centrifugal force was called the sedimentation rate, and the sedimentation rate of the silica in the neutralization solution was measured at a speed where the transparency decreased by the sedimentation in comparison to the transparency at 470 nm.

(4) Identifying the Degree of Cross-Linking of the Polymerized Resin

Regarding the polymerized resins respectively prepared by polymerizing the neutralization liquids prepared in the examples and comparative examples, the degree of cross-linking was measured. After immersing 2 g of the polymerized resin having a diameter of 150 to 850 μm or the classified specimen in distilled water for 60 min and filtering the same with a paper filter, the resin was dried in an oven at 100° C. for 12 h and the weight of the remaining resin was measured. The degree of cross-linking of the polymerized resin may be calculated by the following General Equation.

degree of cross-linking of the polymerized resin (%)=weight of the remaining resin(g)*100/ weight of the used resin(g)  [General Equation]

TABLE 2

| | Transparency (%) | Sedimentation rate (μm/s) | Degree of cross-linking (%) |
|---|---|---|---|
| Example 5 | 90 | 0 | 55 |
| Example 6 | 90 | 0 | 68 |
| Example 7 | 71 | 0.28 | 89 |
| Example 8 | 84 | 0 | 81 |
| Example 9 | 59 | 5.50 | 79 |
| Example 10 | 36 | 3.14 | 75 |
| Comparative Example 3 | 69 | 110 | 25 |

As shown in Tables 1 and 2, it is recognized that the transparency of the inorganic nanoparticles increased and the sedimentation rate became low because the surface thereof was modified with the reactive functional groups and their dispersity increased. Furthermore, the inorganic nanoparticles of which the surface thereof was modified was chemically cross-linked with the SAP and thus the degree of cross-linking increased.

(5) Centrifuge Retention Capacity (CRC)

Regarding the SAPs of the examples and comparative examples, the centrifuge retention capacity (CRC) by absorption ratio under a non-loading condition was measured according to the EDANA (European Disposables and Nonwovens Association) method WSP 241.2.

That is, after inserting $W_0$ (about 0.2 g) of each polymer obtained in the examples and comparative examples uniformly in a nonwoven fabric envelope and sealing the same, it was soaked in a 0.9 wt % saline solution at room temperature. After 30 min, it was dehydrated by using a centrifuge at 250 G for 3 min, and the weight $W_2$ (g) of each envelope was measured. Further, after carrying out the same operation without using the resin, the weight $W_1$ (g) of each envelope was measured.

CRC (g/g) was calculated by using the obtained weight values according to the following Calculation Equation 1, and the water retention capacity was identified.

$$CRC(g/g) = \{[W_2(g) - W_1(g)]/W_0(g)\} - 1 \quad \text{[Calculation Equation 1]}$$

In Calculation Equation 1, $W_0(g)$ is the initial weight (g) of the SAP, $W_1(g)$ is the weight of the apparatus measured after dehydrating the same by using a centrifugal separator at 250 G for 3 min without using the SAP, and $W_2(g)$ is the weight of the apparatus including the SAP measured after soaking the SAP in a 0.9 wt % saline solution for 30 min at room temperature and dehydrating the same by using a centrifugal separator at 250 G for 3 min.

(6) Gel Strength

Regarding the SAPs of the examples and comparative examples, the horizontal direction gel strength was measured.

First, 0.5 g of the SAP specimens of the examples and comparative examples were respectively weighed after sieving the same (at 30-50 mesh). Each weighed specimen was sufficiently swelled in 50 g of saline solution for 1 h. The solvent not absorbed therein was removed by using an aspirator for 4 min, and the solvent left on the surface of the same was evenly distributed and wiped once with a filter paper.

2.5 g of the swelled SAP was loaded between two parallel plates (25 mm diameter, a lower plate thereof having a wall with a 2 mm height for preventing the sample from leaking) of a rheometer, and the gap between the parallel plates was adjusted to 1 mm. The gap between the parallel plates was then adjusted by pressing the plates with a force of about 3 N so that the swelled SAP specimen evenly contacted the faces of the plates.

The shear strain in the linear viscoelastic regime section where the storage modulus (G') and the loss modulus (G") were steady was checked by using the rheometer while increasing the shear strain at the oscillation frequency of 10 rad/s. Generally, in the case of a swelled SAP, a shear strain of 0.1% is in a linear viscoelastic state interval.

The storage modulus and the loss modulus of the swelled SAP were respectively measured by using the shear strain value in the linear viscoelastic state interval at the constant oscillation frequency of 10 rad/s for 60 s. The horizontal direction gel strength was obtained by taking an average of the obtained storage modulus values. For reference, the measured loss modulus was very small, in comparison to the storage modulus.

(7) Water Absorption Per Unit Weight $W_0$ (about 0.2 g) of the resins of the examples and comparative examples were immersed in distilled water at room temperature. After 30 min, each was dehydrated for 3 min, and the weight $W_2$ (g) of the envelope was measured.

The water absorption (g/g) was calculated according to the following Calculation Equation 1 by using the weight thusly obtained.

$$\text{Water absorption}(g/g) = W_1(g)/W_0(g) \quad \text{[Calculation Equation 1]}$$

In Calculation Equation 1, $W_0(g)$ is the initial weight (g) of the SAP, and $W_1(g)$ is the weight (g) of the SAP measured after immersing it in distilled water for 30 min and dehydrating the same for 3 min.

The properties of the SAPs of the examples and comparative examples measured by the above methods are listed in Tables 3 to 5.

TABLE 3

|  | Water absorption (g/g) |
| --- | --- |
| Example 5 | 171 |
| Example 6 | 177 |
| Example 8 | 246 |
| Example 9 | 258 |
| Comparative Example 3 | 168 |

TABLE 4

|  | Centrifuge Retention Capacity (CRC) [Unit: g/g] |
| --- | --- |
| Example 1 | 35.6 |
| Example 2 | 41.2 |
| Example 3 | 32.5 |
| Example 4 | 31.1 |
| Comparative Example 1 | 55.0 |
| Comparative Example 2 | 43.3 |

TABLE 5

|  | Gel Strength [Unit: Pa] |
| --- | --- |
| Example 1 | 3560 |
| Example 2 | 3456 |
| Example 3 | 5517 |
| Example 4 | 5999 |
| Example 5 | 4553 |
| Example 6 | 4078 |
| Example 7 | 5440 |
| Example 8 | 5063 |
| Example 9 | 4572 |
| Example 10 | 4782 |
| Comparative Example 1 | 510 |
| Comparative Example 2 | 3310 |

As shown in Tables 3 to 5, the comparative examples showed an inverse relationship between the water retention capacity and the absorption ability under pressure, in accordance with the content of the inner cross-linking agent, but the examples showed the water retention capacity that was maintained almost as it was or rather increased and more improved absorption performance, in spite of the increase of the content of the inner cross-linking agent, and the gel strength thereof also was higher than that of the comparative examples. That is, it is recognized that the SAP showing an excellent characteristics in which both of the water retention capacity and the absorption ability under pressure are improved together can be provided.

The invention claimed is:

1. A superabsorbent polymer, including: a base resin powder including a 1st cross-linked polymer of a water-soluble ethylenic unsaturated monomer having acid groups of which at least a part is neutralized; and a cross-linked surface layer that includes a 2nd cross-linked polymer further cross-linked from the 1st cross-linked polymer and formed on the base resin powder, wherein an inorganic particle is chemically bonded to the 1st cross-linked polymer by the medium of a cross-linking bond, an oxygen-containing bond (—O—), or a nitrogen-containing bond (—NR—, where R is hydrogen or a $C_1$-$C_3$ alkyl or amide bond).

2. The superabsorbent polymer according to claim 1, wherein the water-soluble ethylenic unsaturated monomer includes one or more monomers selected from the group consisting of: an anionic monomer of acrylic acid, methacrylic acid, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, or 2-(meth)acrylamide-2-methyl propane sulfonic acid, and a salt thereof; a nonionic hydrophilic monomer of (meth)acrylamide, N-substituted (meth)acrylate, 2-hydroxyethyl(meth)acrylate, 2-hydroxypropyl(meth)acrylate, methoxy polyethyleneglycol(meth)acrylate, or polyethyleneglycol (meth)acrylate; and an amino-containing unsaturated monomer of (N,N)-dimethylaminoethyl (meth)acrylate, or (N,N)-dimethylaminopropyl (meth)acrylamide, and a quaternary compound thereof.

3. The superabsorbent polymer according to claim 1, wherein the 1st cross-linked polymer includes a cross-linked polymer prepared by polymerizing the water-soluble ethylenic unsaturated monomer in the presence of an inner cross-linking agent including a multi-functional acrylate-based compound having a plurality of ethylene oxide groups.

4. The superabsorbent polymer according to claim 1, wherein the 1st cross-linked polymer includes a cross-linked structure in which the polymer chains polymerized from the water-soluble ethylenic unsaturated monomer are cross-linked with the cross-linkable functional group of the inner cross-linking agent by the medium of a cross-linking bond, an oxygen-containing bond, or a nitrogen-containing bond of the inorganic particle.

5. The superabsorbent polymer according to claim 3, wherein the inner cross-linking agent includes one or more compounds selected from the group consisting of polyethyleneglycol diacrylate (PEGDA), glycerin diacrylate, glycerin triacrylate, unmodified or ethoxylated trimethylol triacrylate (TMPTA), hexanediol diacrylate, and triethyleneglycol diacrylate.

6. The superabsorbent polymer according to claim 1, wherein the inorganic particle is a silica nanoparticle or an alumina nanoparticle.

7. The superabsorbent polymer according to claim 1, wherein the inorganic particle is surface-modified with a cross-linkable or hydrophilic functional group including at least one functional group selected from the group consisting of a (meth)acrylate-based functional group, an allyl group, a vinyl group, an epoxy group, a hydroxy group, an isocyanate group, and an amine group.

8. The superabsorbent polymer according to claim 1, wherein the 2nd cross-linked polymer includes a polymer that is formed by further cross-linking the 1st cross-linked polymer with a surface cross-linking agent.

9. The superabsorbent polymer according to claim 8, wherein the surface cross-linking agent includes one or more compounds selected from the group consisting of ethyleneglycol, 1,4-butanediol, 1,6-hexanediol, polypropyleneglycol, 1,2-hexanediol, 1,3-hexanediol, 2-methyl-1,3-propanediol, 2,5-hexanediol, 2-methyl-1,3-pentanediol, 2-methyl-2,4-pentanediol, tripropyleneglycol, glycerol, ethylene carbonate, and propylene carbonate.

10. The superabsorbent polymer according to claim 1, wherein the centrifuge retention capacity (CRC) to a saline solution is 20 to 40 g/g, the absorption ability under pressure (0.7 psi) (AUP) to a saline solution is 15 to 35 g/g, and the gel strength is 4000 to 20000 Pa.

11. The superabsorbent polymer according to claim 1, wherein 0.01 to 30 parts by weight of the inorganic particle is bonded to 100 parts by weight of the base resin powder.

12. The superabsorbent polymer according to claim 1, having a particle diameter of 150 to 850 µm.

13. A method of preparing the superabsorbent polymer of claim 1, including the steps of: preparing a hydrogel polymer by carrying out cross-linking polymerization of a water-soluble ethylenic unsaturated monomer having acid groups of which at least a part is neutralized, in the presence of an inner cross-linking agent and an inorganic particle of which the surface is modified with a cross-linkable or hydrophilic functional group including at least one functional group selected from the group consisting of a (meth)acrylate-based functional group, an allyl group, a vinyl group, an epoxy group, a hydroxy group, an isocyanate group, and an amine group; preparing a base resin powder by drying, pulverizing, and classifying the hydrogel polymer; and forming a cross-linked surface layer by further cross-linking the surface of the base resin powder in the presence of a surface cross-linking agent.

14. The method of preparing the superabsorbent polymer of claim 13, wherein 2 to 200 functional groups per inorganic particle are introduced to the surface-modified inorganic particle.

15. The method of preparing the superabsorbent polymer of claim 13, wherein the inorganic particle has a specific surface area of 5 to 600 m2/g and a diameter of 5 to 500 nm.

16. The method of preparing the superabsorbent polymer of claim 13, wherein the surface-modified inorganic particle includes the inorganic particle of which the surface is bonded to the compound of Chemical Formula 1:

[Chemical Formula 1]

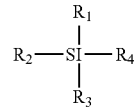

wherein, in Chemical Formula 1, $R_1$ to $R_3$ are independently a $C_1$ to $C_{10}$ alkyl group, a $C_1$ to $C_{10}$ alkoxy group, or a halogen, and at least one of them is not an alkyl group, $R_4$ is a $C_2$ to $C_{20}$ aliphatic functional group including at least one functional group selected from the group consisting of a (meth)acrylate-based functional group, an allyl group, a vinyl group, an epoxy group, a hydroxy group, an isocyanate group, and an amine group at the end, or a $C_2$ to $C_{20}$ hetero-aliphatic functional group of which at least one carbon is substituted with oxygen or nitrogen, including at least one functional group selected from the group consisting of a (meth)acrylate-based functional group, an allyl group, a vinyl group, an epoxy group, a hydroxy group, an isocyanate group, and an amine group at the end.

* * * * *